US00PP23010P2

(12) United States Plant Patent
Bergman

(10) Patent No.: US PP23,010 P2
(45) Date of Patent: Sep. 4, 2012

(54) ***CHRYSANTHEMUM* PLANT NAMED 'CIDZ0001'**

(50) Latin Name: *Chrysanthemum×morifolium*
Varietal Denomination: CIDZ0001

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/135,964

(22) Filed: Jul. 19, 2011

(51) Int. Cl.
*A01H 5/00* (2006.01)

(52) U.S. Cl. ..... Plt./289

(58) Field of Classification Search ..... Plt./289
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0001' particularly distinguished by the large yellow ray floret color with a decorative inflorescence form, strong peduncles, very greyed-green foliage, and a compact growth habit.

1 Drawing Sheet

Latin name of the genus and species of the plant claimed: *Chrysanthemum×morifolium.*

Varietal denomination: 'CIDZ0001'.

BACKGROUND OF THE NEW PLANT

The present invention comprises a new *Chrysanthemum*, botanically known as *Chrysanthemum×morifolium*, and hereinafter referred to by the variety name 'CIDZ0001'.

'CIDZ0001' is a product of a planned breeding program. The new cultivar has large yellow ray floret color with a decorative inflorescence form, strong peduncles, very greyed-green foliage, and a compact growth habit.

'CIDZ0001' originated from a hybridization made in November 1999 in a controlled breeding environment in Salinas, Calif., USA. The female parent was the proprietary plant designated 'YB-6177', unpatented, with yellow ray floret color, that are incurved and a decorative spoon shaped.

The male parent of 'CIDZ0001' was an unpatented plant identified as 'YB-4206' with pink ray floret color, flatter shape, and with an open centered inflorescence. The resultant seed was sown in July 2000 in Fort Myers, Fla. USA.

'CIDZ0001' was selected as one flowering plant within the progeny of the stated cross in November 2000 in a controlled environment in Fort Myers, Fla. USA.

The first act of asexual reproduction of 'CIDZ0001' was accomplished when vegetative cuttings were propagated from the initial selection in March 2001 in a controlled environment in Fort Myers, Fla. USA.

BRIEF SUMMARY OF INVENTION

Horticultural examination of plants grown from cuttings of the plant initiated in March 2001, and continuing thereafter, has demonstrated that the combination of characteristics as herein disclosed for 'CIDZ0001' are firmly fixed and are retained through successive generations of asexual reproduction.

'CIDZ0001' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7059). 'CIDZ0001' has not been made publicly available more than-one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0001' with colors being as true as possible with an illustration of this type.

Figure 1:
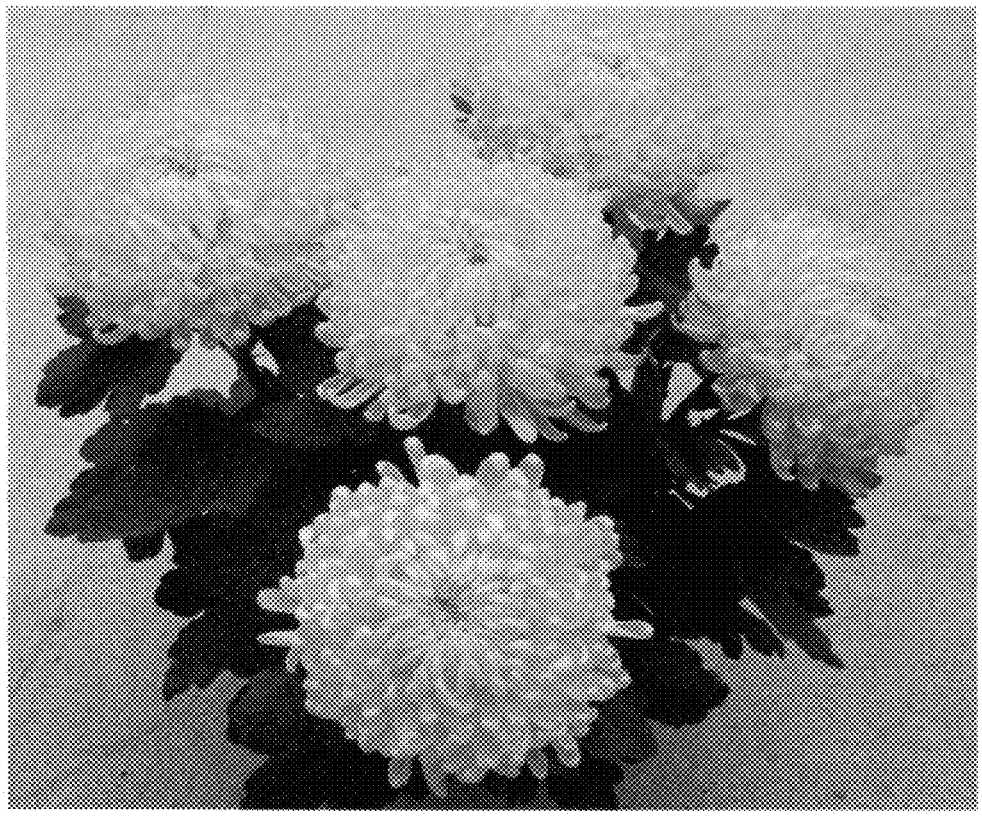
Figure 2:
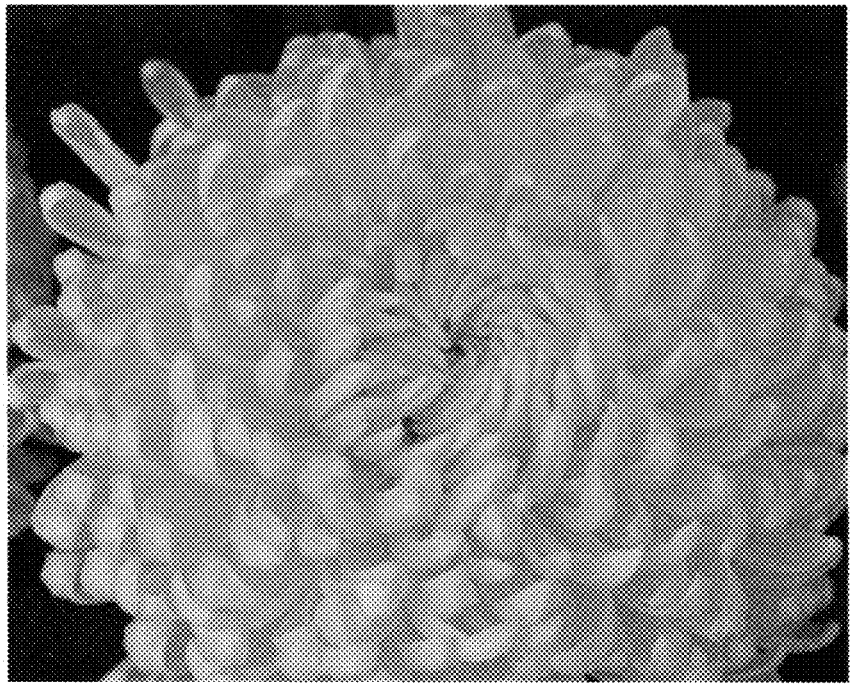

The photographic drawing shows in FIG. 1 five flowering potted plants of the new variety and in FIG. 2 a close-up of the inflorescence.

DETAILED BOTANICAL DESCRIPTION

The plant descriptions, measurements and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age, grown as five plants together in a 6 inch pot under greenhouse trial conditions. Plants were not terminally pinched, but disbudded or removal of all lateral buds, leaving only the terminal buds to develop.

Color references are made to The Royal Horticultural Society Colour Chart (R.H.S.) 2001.

TABLE 1

DIFFERENCES BETWEEN THE NEW VARIETY 'CIDZ0001' AND A SIMILAR VARIETY

| | 'CIDZ0001' | 'Yogolden Gate' (U.S. Plant Pat. No. 17,437) |
|---|---|---|
| Plant habit: | Shorter | Taller |
| Flowering response: | 5-7 days shorter | Faster |

TABLE 1-continued

DIFFERENCES BETWEEN THE NEW VARIETY 'CIDZ0001' AND A SIMILAR VARIETY

| | 'CIDZ0001' | 'Yogolden Gate' (U.S. Plant Pat. No. 17,437) |
|---|---|---|
| Inflorescence diameter: | Larger | Smaller |
| Quantity of ray florets: | About 350 | About 325 |
| Quantity of disc florets: | 60-65 | None observed |

Plant:
- *Form, growth and habit*.—Herbaceous pot-type, strong stems, compact habit.
- *Plant height*.—20.0 cm.
- *Plant height* (*inflorescence included*).—30-31.0 cm.
- *Plant width*.—20.0 cm.

Roots:
- *Number of days to initiate roots*.—About 4 days at about 22 degrees C.
- *Number of days to produce a rooted cutting*.—About 10 days at 22 degrees C.
- *Type*.—Fine, fibrous, free branching.
- *Color*.—RHS N155B but whiter.

Foliage:
- *Arrangement*.—Alternate, simple.
- *Immature, leaf color, upper surface*.—RHS N189A.
- *Lower surface*.—RHS 147B but greyer.
- *Mature, leaf color, upper surface*.—RHS N189A.
- *Lower surface*.—RHS 147B but greyer.
- *Length*.—9.5-11.0 cm.
- *Width*.—7.5-9.9 cm.
- *Shape*.—Ovate.
- *Base shape*.—Attenuate.
- *Apex shape*.—Mucronulate.
- *Margin*.—Palmately lobed; irregularly serrate.
- *Texture, upper surface*.—Bifid T-shaped hairs.
- *Lower surface*.—Bifid T-shaped hairs.
- *Color of veins, upper surface*.—RHS 144A.
- *Color of veins, lower surface*.—RHS 144A.
- *Petiole color*.—RHS 144A.
- *Length*.—2.5-3.5 cm.
- *Diameter*.—0.5 cm.
- *Texture*.—Bifid T-shaped hairs.

Stem:
- *Quantity of main branches per plant*.—1.
- *Color of stem*.—RHS 138A but appears lighter due to hairs.
- *Length of stem*.—20-21.0 cm.
- *Diameter*.—0.7 cm.
- *Length of internodes*.—1.0-1.25 cm.
- *Texture*.—Bifid T-shaped hairs.
- *Color of peduncle*.—RHS 138A but appears lighter due to hairs.
- *Length of peduncle*.—4.0-4.5 cm.
- *Peduncle diameter*.—0.4 cm.
- *Texture*.—Bifid T-shaped hairs.

Inflorescence:
- *Type*.—Compositae type, solitary inflorescences, decorative-type, borne terminally above foliage, ray florets arranged acropetally on a capitulum.
- *Quantity of short days to flowering* (*response time*).—About 4 weeks.
- *Quantity of inflorescences per plant*.—1.
- *Lastingness of individual blooms on the plant*.—About 4 weeks.
- *Fragrance*.—Slightly spicy.

Bud (just when opening/showing color):
- *Color*.—Closest to RHS 3B.
- *Length*.—1.5-2.0 cm.
- *Width*.—2.0-2.2 cm.
- *Shape*.—Oblate.

Immature inflorescence:
- *Diameter*.—0.9-1.2 cm.
- *Color of ray florets, upper surface*.—RHS 6B.
- *Lower surface*.—RHS 4A with RHS 5C in center.

Mature inflorescence:
- *Diameter*.—14-15.0 cm.
- *Depth*.—7.5 cm.
- *Total diameter of 'disc'*.—Visually indistinct.
- *Receptacle height*.—0.6-0.8 cm.
- *Receptacle diameter*.—0.9-1.0 cm.

Ray florets:
- *Average quantity of florets*.—Approximately 350 in numerous whorls.
- *Color of florets, upper surface*.—RHS 6B.
- *Lower surface*.—RHS 4A.
- *Length*.—5.0-6.9 cm.
- *Width*.—0.9 (spoon section)-1.4 cm (open-flat section).
- *Shape*.—Some are slightly spooned, otherwise elliptical.
- *Apex shape*.—Acute to slightly emarginate.
- *Margin*.—Entire.
- *Texture, upper surface*.—Papillose.
- *Lower surface*.—Papillose.

Disc florets:
- *Average quantity of florets*.—Approximately 60-65.
- *Color of florets*.—RHS 1C.
- *Length*.—0.6 cm.
- *Width*.—0.1 cm.
- *Shape*.—Tubular, elongated.
- *Apex shape*.—Acute, 5 pointed.

Phyllaries:
- *Quantity*.—Approximately 40.
- *Color, upper surface*.—RHS 137C.
- *Lower surface*.—RHS 137B but appears lighter due to hairs.
- *Length*.—0.9-1.3 cm.
- *Width*.—0.2-0.4 cm.
- *Shape*.—Lanceolate.
- *Apex shape*.—Acute.
- *Based*.—Fused.
- *Margins*.—Entire; papery.
- *Texture, upper surface*.—Glabrous.
- *Lower surface*.—Bifid T-shaped hairs.

Reproductive organs:
- *Pistil*.—1.
- *Found on both florets*.—Yes.
- *Length*.—0.6-0.8 cm.
- *Style color*.—RHS 1C.
- *Style length*.—0.5-0.7 cm.
- *Stigma color*.—RHS 9A.
- *Stigma shape*.—Bi-parted.
- *Ovary color*.—Not observed.
- *Stamens*.—4.
- *Found on only disc florets*.—Yes.
- *Color of filaments*.—RHS 1C.
- *Length filaments*.—0.2-0.3 cm.
- *Anther color*.—RHS 9B.
- *Anther length*.—0.1 cm.
- *Anther shape*.—Oblong.

*Color of pollen*.—Not observed.

*Pollen amount*.—Not observed.

*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'CIDZ0001' substantially as illustrated and described herein.

* * * * *